United States Patent [19]

Chekroun et al.

[11] Patent Number: 4,493,931

[45] Date of Patent: Jan. 15, 1985

[54] PROCESS FOR THE PREPARATION OF β-CYCLO-SUBSTITUTED ETHYLAMINES

[75] Inventors: Isaac Chekroun, Toulouse; Alain Heymes, Sisteron, both of France

[73] Assignee: Sanofi, Toulouse, France

[21] Appl. No.: 393,383

[22] Filed: Jun. 29, 1982

[30] Foreign Application Priority Data

Jun. 30, 1981 [FR] France ............... 81 13065

[51] Int. Cl.³ .................. C07D 213/18; C07C 85/24; C07C 87/28; C07C 333/28
[52] U.S. Cl. ................................ 546/329; 564/374; 564/378; 260/465 E; 562/442; 549/65; 549/492
[58] Field of Search .............. 564/374, 378; 546/329; 549/65, 492; 562/442; 260/465 E

[56] References Cited

U.S. PATENT DOCUMENTS 4,051,141  9/1977  Castaigne .................. 546/114
4,097,482  6/1978  Amselem .................... 546/114

Primary Examiner—Alan L. Rothman
Attorney, Agent, or Firm—Weiser & Stapler

[57] ABSTRACT

The present invention provides a multistep process for the preparation of β-cyclo-substituted ethylamines of the general formula:-

$$Ar-CH_2-CH_2-NH_2 \qquad , (I)$$

in which AR is a heterocyclic or non-heterocyclic aromatic radical, which is optionally mono- or poly- substituted, wherein said compounds represent a class of intermediates which can be converted to 4,5,6,7-tetrahydro[3,2-C] or [2,3-C]pyridines wherein the latter are useful for anti-inflammatory, vasodilator or blood platelet aggregation inhibition activities.

11 Claims, No Drawings

PROCESS FOR THE PREPARATION OF β-CYCLO-SUBSTITUTED ETHYLAMINES

The present invention is concerned with a new process for the preparation of β-cyclo-substituted ethylamines.

The β-cyclo-substituted ethylamines with which the present invention is concerned are compounds of the general formula:

Ar—CH₂—CH₂—NH₂    (I)

in which Ar is a heterocyclic or non-heterocyclic aromatic radical, such as thienyl, furfuryl, pyridyl, phenyl or naphthyl radical, optionally mon- or poly-substituted by substituents such as halogen, nitro, amino, cyano, carboxyl, alkyl, halogenalkyl, alkoxy, halogenalkoxy or phenyl groups.

A large number of derivatives corresponding to general formula (I) are known and used as intermediates in the preparation of compounds employed both in the chemical industry and in the pharmaceutical industry.

Thus, by way of example, amongst the derivatives obtained in accordance with the new process, there may be mentioned 2-(thien-2-yl)-ethylamines and 2-(thien-3-yl)-ethylamines, which, by known means which are easy to carry out (cf. S. Gronowitz and E. Sandberg, Arkiv. Kemi, 32, 217/1970), lead respectively, to 4,5,6,7-tetrahyrothieno[3,2-c]pyridines and 4,5,6,7-tetrahydrothieno[2,3-c]pyridines, some derivatives of which have formed the subject of several of our earlier French patents (Nos. 73/03,503, 75/03,968, 75/20,241, 75/23,786, 75/24,486, 76/00,003 and 77/21,517) for their therapeutic use and/or processes for their preparation.

The present invention provides a process, which is simple and inexpensive compared with the prior art, for the preparation of compounds of general formula (I).

According to the process of the present invention, in order to prepare compounds of general formula (I):

(a) a compound of the general formula:

in which X and Y, which may be the same or different, are alkyl, aryl, alkoxy, aryloxy, dialkylamino or diarylamino radicals so that the organophosphorus compound of general formula (II) can be, for example, a phosphonate, a phosphinate, a phosphine oxide or a phosphonamide, is condensed with a carbonyl compound of the general formula:

AR—CHO    (III)

in which Ar is as defined in general formula (I), to give a compound of the general formula:

in which the various symbols have the meanings given above;

(b) a compound of general formula (IV) is treated with a base of the general formula B⊖M⊕ to give a carbanion of the general formula:

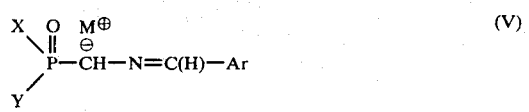

in which the various symbols have the meanings given above;

(c) the carbanion of general formula (V) is converted by the action of heat into a compound of the general formula:

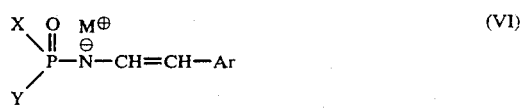

in which the various symbols have the meanings given above, in order to give, after taking up in water, a compound of the general formula:

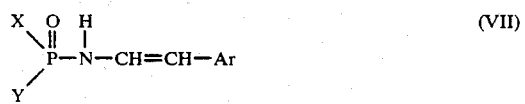

in which the various symbols have the meanings given above, this reaction generally being carried out at a temperature of from −78° C. to +150° C. which is chosen, more specifically, as a function of the base B⊖M⊕, to be on the whole at the top of the range, especially when carrying out stage c);

(d) the compound of general formula (VII) is converted into a compound of the general formula:

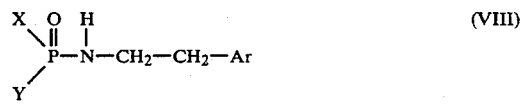

in which the various symbols have the meanings given above, by reaction with a reducing agent;

(e) the compound of general formula (VIII) is finally reacted with an acid agent in order to give a derivative of general formula (I) as defined above.

The process of preparation according to the present invention can be illustrated by the following reaction scheme:

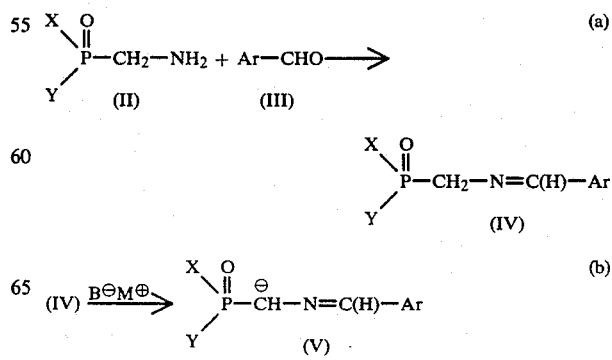

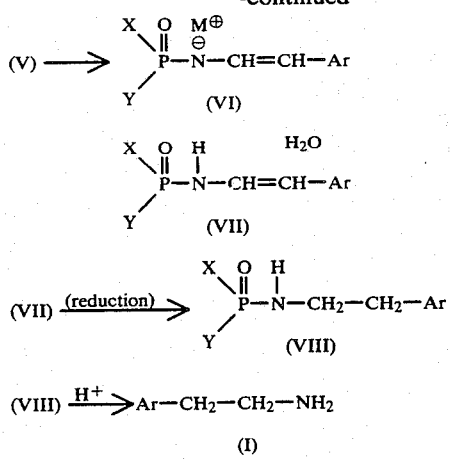

$$(V) \longrightarrow \underset{Y}{\overset{X}{\diagdown}}P-\underset{|}{N}-CH=CH-Ar \quad (VI)$$

$$\underset{Y}{\overset{X}{\diagdown}}\overset{O}{\underset{\|}{P}}-\underset{|}{\overset{H}{N}}-CH=CH-Ar \quad (VII)$$

$$(VII) \xrightarrow{(reduction)} \underset{Y}{\overset{X}{\diagdown}}\overset{O}{\underset{\|}{P}}-\underset{|}{\overset{H}{N}}-CH_2-CH_2-Ar \quad (VIII)$$

$$(VIII) \xrightarrow{H^+} Ar-CH_2-CH_2-NH_2 \quad (I)$$

The process can advantageously be carried out as follows:

(a) The organophosphorus compounds of general formula (II), which are readily obtainable by well-known processes of preparation, such as the one described by I. C. Popoff et al. (J. Org. Chem., 28, 2898/1963), can be reacted with the carbonyl derivatives (III) in the absence of a solvent and of a catalyst, the water formed during the reaction being removed at the end of the operation by appropriate means. The condensation can advantageously be carried out in a solvent, such as an aromatic hydrocarbon, for example toluene, or an alcohol, for example ethanol, by means of which it is possible to remove the water by azeotropic distillation. It can also be advantageous (from the point of view of the speed) to carry out the condensation in the presence of a catalytic amount of a mineral or organic acid, for example, p-toluenesulphonic acid. The temperature at which this conversion is carried out can vary but is very generally from 20° to 120° C.

(b) The base $B^{\ominus}M^{\oplus}$ used in this stage can be an alkali metal hydride, especially sodium, lithium or potassium hydride, an alkali metal amide or alkylamide, especially an alkali metal dialkylamide, such as lithium diisopropylamide, or an organometallic compound, especially an organolithium, such as n-butyllithium, or an organosodium or organo magnesium. It is also possible to use alkali metal or alkaline earth metal alcoholates, such as sodium, lithium, potassium or magnesium methylate, potassium tert.-butylate or sodium tert.-amylate. It is also possible to use alkali metal or alkaline earth metal hydroxides, such as sodium, lithium, potassium or magnesium hydroxide.

In general, one stoichiometric equivalent of the base $B^{\ominus}M^{\oplus}$, or even a slight excess, for example an excess of 10%, relative to equivalence, is used. However, it is also possible to use amount of base which are less or even substantially less than stoichiometric equivalence.

The reaction is generally carried out at a temperature of from −78° C. to +150° C., the temperature being chosen, more specifically, as a function of the base $B^{\ominus}M^{\oplus}$, to be on the whole at the top of the range, especially when carrying out stage (c).

The preferred solvents are linear or cyclic ethers, such as tetrahydrofuran, hydrocarbons, especially aromatics, such as benzene, toluene and xylenes, alcohols, amides, especially dimethylformamide, and sulphoxides, especially dimethyl sulphoxide. It can also be advantageous, especially when using metal hydroxides, to carry out the reaction in a two-phase system (water+a solvent, such as a halogen-containing solvent, for example methylene chloride, or an aromatic hydrocarbon, for example benzene, toluene or xylenes) in the presence of a phase-transfer catalyst, especially a quaternary ammonium salt, such as tetra-n-butyl-ammonium iodide, or a phosphonium salt. The usual treatment makes it possible to isolate the compound (V).

(c) The reduction of the derivatives of general formula (V) is advantageously carried out with a mixed alkali metal hydride, especially a borohydride, for example sodium or potassium borohydride. The reduction is carried out in an inert solvent, such as an ether, for example tetrahydrofuran or dioxan, or in an alcohol, for example methanol or ethanol.

It is also possible to carry out this reduction by means of catalytic hydrogenation in a homogeneous or heterogeneous phase, under conditions which are generally well known.

(d) The acid-catalysed splitting of the phosphorus-nitrogen bond in the compounds (VI) can be carried out by using a mineral acid, such as a hydrohalic acid, for example hydrochloric acid or hydrobromic acid, but also an organic acid, especially a strong acid, such as a sulphonic acid, for example benzenesulphonic acid or p-toluenesulphonic acid. The preferred solvents include ethers, especially cyclic ethers, such as tetrahydrofuran or dioxan, alcohols, such as methanol or ethanol, amides, especially dimethylformamide, and sulphoxides, especially dimethyl sulphoxide. It is possible to carry out the reaction in these solvents in the absence of water but also in mixtures containing variable amounts of water. Finally, it is also possible to carry out the reaction in water itself.

In general, one to two stoichiometric equivalents of acid are used. The reaction is generally carried out at a temperature of from 0° to 100° C. and particularly of from 30° to 70° C. The compounds of general formula (I) thus obtained can then be isolated and purified in accordance with the usual methods. To carry out these operations, it can be advantageous to convert the free bases of general formula (I) into their salts, for example into their acid-addition salts by reaction with mineral or organic acids. The compounds of general formula (I) can be liberated from their salts by known methods.

The present invention also includes the intermediates obtained at the various stages of the synthesis: compounds of the general formula:

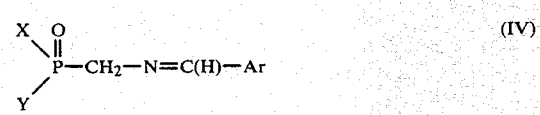

(IV)

compounds of the general formula:

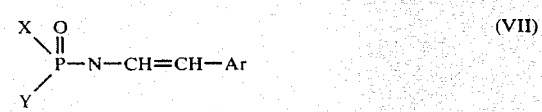

(VII)

compounds of the general formula:

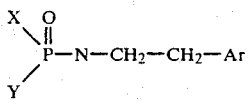

(VIII)

and compounds of the general formula:

Ar—CH₂—CH₂—NH₂  (I)

The following Examples are given for the purpose of illustrating the present invention:

EXAMPLE 1

Preparation of 2-(thien-2-yl)-ethylamine hydrochloride

Stage a

Diethyl N-(thien-2-ylidene)-aminomethylphosphonate

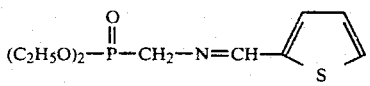

11.2 g. (0.1 mol) Thien-2-aldehyde are added to 16.7 g. (0.1 mol) diethyl aminomethylphosphonate in 200 ml. absolute ethanol and the mixture is heated under reflux for 30 minutes. The water formed during the reaction is removed by azeotropic distillation. After complete evaporation of the solvent, 28 g. (about 100%) of a yellow oil are collected, which is pure according to LC, TLC and GC.

IR (film) C=N 1645 cm⁻¹, P—O 1260 cm⁻¹, P—O—C 1060-1080 cm⁻¹,

NMR (CDCl₃) δ/TMS 1.3 ppm (t, 6H), 3.9 to 4.45 ppm (m, 6H), 7 to 7.6 ppm (m, 3H), 8.5 ppm (d, 1H).

Stages b and c

Diethyl N-[β-(thien-2-yl)-vinyl]-phosphoramidate

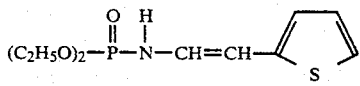

A solution of 27.9 g. (0.1 mol) diethyl N-(thien-2-ylidene)-aminomethylphosphonate in 40 ml. tetrahydrofuran is added dropwise to a suspension of 11.2 g. (0.1 mol) potassium tert.-butylate in 160 ml. tetrahydrofuran. During the addition, the temperature rises from 20° to 35° C. When the addition has ended, the temperature is raised to 40°-45° C. for 30 minutes and the reaction mixture is then poured into 400 ml. of a saturated aqueous solution of ammonium chloride. The aqueous phase is extracted with diisopropyl ether and the combined ether phases are then washed with a saturated solution of sodium chloride, dried over anhydrous sodium sulphate and evaporated to give 20.9 g. (75%) of the desired product in the form of a yellow oil.

NMR (CDCl₃) δ/TMS 1.3 ppm (t, 6H), 3.95 ppm (dq, 4H), 6.35 ppm (m, 1H), 6.9 to 7.5 ppm (m, 5H) after exchange with D₂O: (m, 4H).

IR (film) NH 3300 cm⁻¹, C=C 1645 cm⁻¹, P—O 1250 cm⁻¹, P—O—C 1050 cm⁻¹.

Stage d

Diethyl N-[2-(thien-2-yl)-ethyl]-phosphoramidate

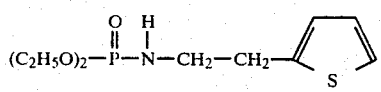

The 20.9 g. (0.075 mol) of diethyl N-[δ-(thien-2-yl)-vinyl]-phosphoramidate obtained above are added to a solution of 5.1 g. (0.075 mol) sodium borohydride in 200 ml. ethanol. During the addition, the temperature rises and then stabilises at 30° C. After stirring for a further 2 hours, the temperature of the mixture is raised to 45°-50° C. for 1 hour, the ethanol is then evaporated off and the residue is taken up in a mixture of diisopropyl ether and water. The aqueous phase is re-extracted several times with diisopropyl ether and the combined organic phases are washed with water, dried over anhydrous sodium sulphate and evaporated to give 21 g. (about 75%, referred to the starting aminomethylphosphonate) of the desired compound in the form of a yellow oil.

IR (film) 3400 cm⁻¹, 1520 cm⁻¹, 1275 cm⁻¹, 1210 cm⁻¹,

NMR (CDCl₃) δ/TMS, 1.3 ppm (t, 6H), 3.1 ppm (m, 5H) Ar—CH₂—CH₂—NH (Exchange with D₂O gives: 3.1 ppm (m, 4H)), 4.05 ppm (dq, 4H), 6.75 to 7.2 ppm (m, 3H).

Stage e 2-(Thien-2-yl)-ethylamine hydrochloride

A well-stirred mixture of 21 g. of the phosphoramidate obtained above and 100 ml. of a 6N aqueous solution of hydrochloric acid is heated at 80° to 85° C. for 1.5 hours. After cooling and extraction of the reaction mixture with 30 ml. methylene chloride, the isolated aqueous phase is rendered basic with an aqueous solution of sodium hydroxide and then extracted with diisopropyl ether.

The ether phase is isolated and then dried over anhydrous sodium sulphate, whereafter hydrogen chloride is bubbled in: this brings about the precipitation of crystals which are filtered off and purified by dissolving in ethanol and then reprecipitating by adding diisopropyl ether. 8.9 g. (overall yield: 54%) 2-(thien-2-yl)-ethylamine hydrochloride are obtained in the form of white crystals; m.p. 202° C.

NMR (D₂O) 3.25 ppm (s, 4H), 7 ppm (m, 2H), 7.35 ppm (m, 1H) water peak at 4.65 ppm.

IR (KBr disc) 3000 cm⁻¹, 1590 cm⁻¹, 1470 cm⁻¹, 1230 cm⁻¹,

Analysis: C₆H₁₀NS.HCl (M.W. 164.679) calculated: C 43.75%; H 6.73%; N 8.50%; found: 43.70%; 6.77%; 8.45%.

EXAMPLE 2

Preparation of 2-phenylethylamine hydrochloride

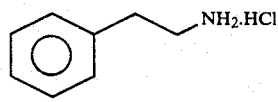

Stage a

Diethyl N-(benzylidene)-aminomethylphosphonate

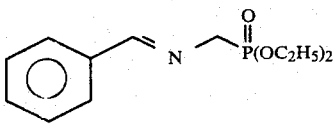

The above imine is obtained in 100% yield by reacting 0.1 mol (16.7 g.) diethyl aminomethyl phosphonate with 10.6 g. (0.1 mol) benzaldehyde under the same conditions as those described in Example 1. The product obtained is a light yellow oil.

NMR (CDCl$_3$) δ/TMS 1.3 ppm (t, 6H), 4 ppm (m, 6H), 7.2 to 7.8 ppm (m, 5H), 8.2 ppm (d, 1H), IR (film) C=N 1640 cm$^{-1}$, P—O 1250 cm$^{-1}$,

Stages b and c

Diethyl N-(β-phenylvinyl)-phosphoramidate

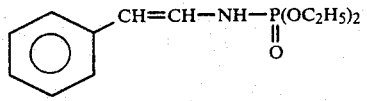

35.7 ml. (0.1 mol) of a 2.8M solution of n-butyllithium in cyclohexane are added dropwise to a solution of 25.5 g. (0.1 mol) diethyl N-benzylidene-aminomethylphosphonate in 200 ml. tetrahydrofuran kept at 20° C. When the addition has ended, the reaction mixture is heated to 35° C., kept at this temperature for 30 minutes, then poured into 1 liter of a saturated aqueous solution of ammonium chloride and finally extracted with diisopropyl ether. The ether phase is washed with water, dried over anhydrous sodium sulphate and evaporated to give a yellow oil which solidifies upon trituration in hexane. After filtration and recrystallisation from hexane, the crystals obtained are washed with a hexane/diisopropyl ether mixture (90/10 v/v) and then dried in vacuo at ambient temperature to give 17.9 g. (70%) diethyl N-(β-phenylvinyl)-phosphoramidate; m.p. 60° C.

IR (KBr disc) NH 3400 cm$^{-1}$, CH=CH 1650 cm$^{-1}$, P—O 1250 cm$^{-1}$.

NMR (CDCl$_3$) δ/TMS, 1.3 ppm (t, 6H), 4.05 ppm (dq, 4H), * 5.85 ppm (dd, 1H), J$_1$=13 Hz, ** 6.65 ppm (m, 2H), J$_2$=6 Hz, 7.15 ppm (s, 5H), after exchange with D$_2$O: * 5.85 (d, 1H) J=13 Hz ** 6.65 (dd, 1H), J$_1$=13 Hz, J$_2$=16 Hz.

Analysis: C$_{12}$H$_{18}$NO$_3$P (M.W. 255.243) calculated: C 56.46%; H 7.10%; N 5.48%, found: 56.10%; 7.20%; 5.50%.

Stage d

Diethyl N-(2-phenylethyl)-phosphoramidate

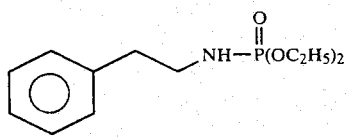

12.75 g. (0.05 mol) of the N-vinylphosphoramidate prepared in stages (b) and (c) are reduced with sodium borohydride in ethanol, under the conditions described in Example 1 to give 12.85 g. (yield of the reduction: 100%) of the desired phosphoramidate in the form of a light yellow oil.

IR (film) 3200 cm$^{-1}$, 2900 cm$^{-1}$, 1475 cm$^{-1}$, 1275 cm$^{-1}$, 1220 cm$^{-1}$.

NMR (CDCl$_3$) δ/TMS, 1.33 ppm (t, 6H), about 3 ppm (m, 5H), 1H exchangeable with D$_2$O, 4 ppm (qd, 4H), 7.2 ppm (s, 5H).

Stage e

2-Phenylethylamine hydrochloride 12.85 g. (0.05 mol) of the phosphoramidate prepared above are treated with a 6N aqueous solution of hydrochloric acid under the conditions described in Example 1. The amine is isolated and then converted to the hydrochloride in diisopropyl ether. This gives 7.5 g. 2-phenylethylamine hydrochloride in the form of white crystals (yield: 95%, referred to the phosphoramidate precursor and an overall yield from the diethyl aminomethylphosphonate of 66.5%); m.p. 222° C.

IR (film, on the base) 3400 cm$^{-1}$, 3000 cm$^{-1}$, 2900 cm$^{-1}$, 1600 cm$^{-1}$, 1490 cm$^{-1}$, 1450 cm$^{-1}$, 820 cm$^{-1}$, 725 cm$^{-1}$, 700 cm$^{-1}$.

NMR (CDCl$_3$, on the base) δ/TMS, 2.8 ppm (m, 4H), 7.2 ppm (s, 5H), 1.1 ppm (s, 2H), exchangeable with D$_2$O, Analysis: C$_8$H$_{11}$.HCl (M.W. 157.643) calculated: C 60.94%; H 7.67%; N 8.88%, found: 61.01%; 7.70%; 8.85%.

EXAMPLE 3

Preparation of 2-phenylethylamine hydrochloride

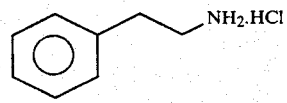

Stage a

Diisopropyl N-benzylidene-aminomethylphosphonate

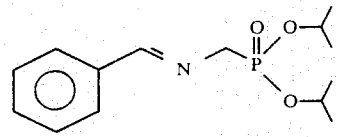

The desired imine is obtained in a quantitative yield by reacting 10.6 g. (0.1 mol) benzaldehyde with 19.5 g. (0.1 mol) diisopropyl aminomethylphosphonate under the conditions described in Example 1.

IR (film) C=N 1640 cm$^{-1}$ P—O 1250 cm$^{-1}$

NMR (CDCl$_3$) δ/TMS 1.35 ppm (d, 12HO, 3.95 ppm (d, 2H), 4.5 ppm (m, 2H), 7.2 to 7.8 ppm (m, 5H), 8.2 ppm (d, 1H).

Stages b and c

Diisopropyl N-(β-phenylvinyl)-phosphoramidate

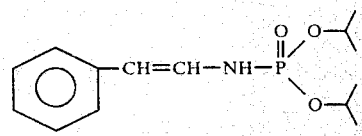

35.7 ml. (0.1 mol) of a 2.8M solution of n-butyllithium in hexane are added dropwise at 20° C. to a solution of 28.3 g. (0.1 mol) diisopropyl N-benzylideneaminomethylphosphonate in 200 ml. tetrahydrofuran. After the addition has ended, the reaction medium is heated at 35° C. for 30 minutes and then hydrolysed and the aqueous phase is extracted with diisopropyl ether. The ether phase is dried over anhydrous sodium sulphate and then evaporated, a yellow oil being obtained which is triturated in hexane to give 21.2 g. (yield: 75%) of a yellow solid; m.p. 98° C.

NMR (CDCl₃) 1.35 ppm (d, 12H), 4.5 ppm (m, 2H), * 5.80 ppm (dd, 1H), $J_1=13$ Hz, $J_2=6$ Hz, ** 6.65 ppm (m, 2H), 7.15 ppm (s, 5H), after exchange with D₂O: * 5.80 ppm (d, 1H) ** 6.65 ppm (dd, 1H) $J_1=13$ Hz, $J_2=15$ Hz.

IR (KBr disc) 3400 cm⁻¹, 1650 cm⁻¹, 1250 cm⁻¹.

Analysis: $C_{14}H_{22}NO_3P$ (M.W. 283.303) calculated: C 59.34%; H 7.82%; N 4.94%, found: 59.25%; 7.80%; 5.00%.

Stage d

Diisopropyl N-(2-phenylethyl)-phosphoramidate 1.6 g. of the N-vinylphosphoramidate prepared above is dissolved in 80 ml. dioxan and hydrogenated over the course of 6 hours in the presence of 160 mg. of 10% palladium-charcoal at a pressure of 3 bars and a temperature of from 55° to 60° C. After the catalyst has been filtered off and the dioxan has been evaporated off, 1.6 g. (about 100%) of the desired phosphoramidate is obtained in the form of a colourless oil.

NMR (CDCl₃) δ/TMS 1.35 ppm (d, 12H), * 3 ppm (m, 5H), 4.5 ppm (m, 2H), 7.2 ppm (s, 5H), * after exchange with D₂O: 3 ppm (m, 4H)

IR (film) 3250 cm⁻¹, 2900 cm⁻¹, 1475 cm⁻¹, 1275 cm⁻¹, 1220 cm⁻¹.

Stage e

2-Phenylethylamine hydrochloride

A solution of 1.425 g. (5 millimols) diisopropyl N-(2-phenylethyl)-phosphoramidate in 20 ml. diisopropyl ether saturated with hydrogen chloride is stirred overnight at ambient temperature. The precipitate of 2-phenylethylamine hydrochloride formed is filtered off, washed with diisopropyl ether and then dried in vacuo to give 0.75 g. (yield: 95%) of a crystalline solid, the physical and spectral characteristics of which are identical to those of the compound prepared in Example 2.

EXAMPLE 4

Preparation of 2-(5-bromothien-2-yl)-ethylamine hydrochloride

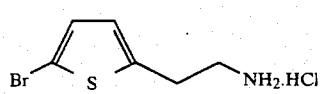

Stage a

Diethyl N-(5-bromothien-2-ylidene)-aminomethylphosphonate

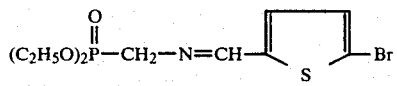

Starting from 16.7 g. (0.1 mol) diethyl aminomethylphosphonate and 19.1 g. (0.1 mol) 5-bromothien-2-aldehyde and following a procedure identical to that described in Example 1, 34 g. (yield: 100%) of the desired product are obtained in the form of a yellow oil.

IR (film) 3000 cm⁻¹, 2900 cm⁻¹, 1630 cm⁻¹, 1430 cm⁻¹, 1250 cm⁻¹, 1050 cm⁻¹,

NMR (CDCl₃) δ/TMS 1.3 ppm (t, 6H), 4.1 ppm (m, 6H), 7 to 7.15 ppm (m, 2H), 8.2 ppm (d, 1H).

Stages b and c

Diethyl N-[β-(5-bromothien-2-yl)-vinyl]-phosphoramidate

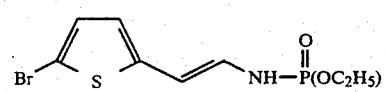

34 g. (0.1 mol) of the imine prepared above and 0.1 mol of potassium tert.-butylate give, under the conditions described in Example 1, 30 g. of the desired product in the form of a yellow-orange oil, which is used as such in the following step.

Stage d

Diethyl N-[2-(5-bromothien-2-yl)-ethyl]-phosphoramidate

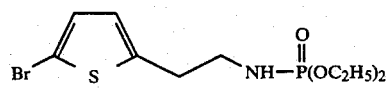

The crude vinylphosphoramidate obtained above in stages (b) and (c) is treated with 3.8 g. (0.1 mol) sodium borohydride under the conditions described in Example 1 to give crude diethyl N-[2-(5-bromothien-2-yl)-ethyl]-phosphoramidate, which is purified by chromatography on a silica column (eluant: ethyl acetate); this gives 17.1 g. of the desired phosphoramidate in the form of a yellow oil (50%, referred to the diethyl aminomethylphosphonate used in stage (a)).

IR (film), 3400 cm⁻¹, 3250 cm⁻¹, 3000 to 2850 cm⁻¹, 1450 cm⁻¹, 1240 cm⁻¹, 1040 cm⁻¹.

| NMR (CDCl₃) | δ/TMS | | |
|---|---|---|---|
| | 1.33 ppm | (t, 6 H) | |
| | *3 ppm | (m, 5 H) | |
| | 4 ppm | (dq, 4 HO) | |
| | 6.55 ppm | (d, 1 H) | ⎫ AB system |
| | | | ⎬ with |
| | 6.80 ppm | (d, 1 H) | ⎭ $J_{AB} = 4$ Hz |

*on exchange with D₂O: (m, 4H)

Stage e

2-(5-Bromothien-2-yl)-ethylamine hydrochloride

A solution containing 3.42 g. (0.01 mol) diethyl N-[2-(5-bromothien-2-yl)-ethyl]-phosphoramidate in 50 ml. diisopropyl ether saturated with hydrogen chloride is stirred overnight at ambient temperature. The crystals formed are filtered off and washed with diisopropyl ether. After drying, there is obtained 1.45 g. (yield: 60%, referred to the phosphoramidate used) of the desired product in the form of silverygrey flakes; m.p. 220° C. (decomposition)

IR (KBr disc), 3400 cm$^{-1}$, 3000 cm$^{-1}$, 1600 cm$^{-1}$, 1450 cm$^{-1}$, 1170–1150 cm$^{-1}$,

| NMR (d$_6$-DMSO) | δ/TMS | |
|---|---|---|
| 3.05 ppm | (s broad, 3 H) | |
| 6.65 ppm | (d, 1 H) | AB system with |
| 6.98 ppm | (d, 1 H) | $J_{AB}$ = 4 Hz |
| 8.4 ppm | (3 H), | exchangeable with D$_2$O |

Analysis: C$_6$H$_8$BrNS.HCl (M.W. 242.58) calculated: C 29.70%; H 3.73%; N 5.77%, found: 29.71%; 3.73%; 5.72%.

EXAMPLE 5

Preparation of 2-(naphth-1-yl)-ethylamine hydrochloride

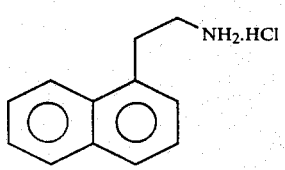

Stage a

Imine of naphth-1-yl-carboxaldehyde and diethyl aminomethylphosphonate

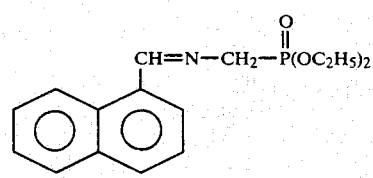

Starting from 15.6 g. (0.1 mol) naphthalene-1-carboxaldehyde and 16.7 g. (0.1 mol) diethyl aminomethylphosphonate, 30.5 g. (yield: 100%) of the desired product are prepared by a procedure identical to that described in Example 1.

IR (film) 3000 cm$^{-1}$, 1640 cm$^{-1}$, 1510 cm$^{-1}$, 1250 cm$^{-1}$, 1030–1050 cm$^{-1}$.

NMR (CDCl$_3$) δ/TMS, 1.3 ppm (t, 6H), 4 ppm (m, 6H), 6.9 to 8.1 ppm (m, 7H), 8.3 ppm (d, 1H),

Stages b and c

Diethyl N-[β-(naphth-1-yl)-vinyl]-phosphoramidate

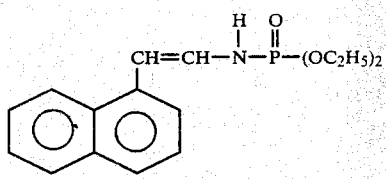

Starting from 30.5 g. (0.1 mol) of the imine prepared in the previous stage and 11.2 g. (0.1 mol) potassium tert.-butylate and using the procedure described in Example 1, 22.3 g. (yield: 73%) of the desired product are obtained in the form of a light yellow oil.

IR (film), 3400 cm$^{-1}$, 3200 cm$^{-1}$, 1650 cm$^{-1}$, 1250 cm$^{-1}$, 1050 cm$^{-1}$.

NMR (CDCl$_3$) δ/TMS, 1.3 ppm (t, 6H), 4.1 ppm (qd, 4H), 6.7 to 6.9 ppm (m, 2H), 7 to 8.1 ppm (m, 8H).

On adding D$_2$O, the spectrum becomes somewhat simpler and the integration decreases.

Stage d

Diethyl N-[2-(naphth-1-yl)-ethyl]-phosphoramidate

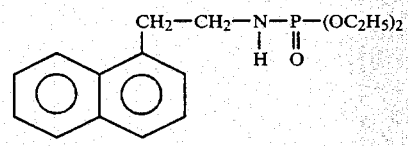

Starting from the 22.3 g. (0.073 mol) of the vinyl-phosphoramidate obtained above and 2.85 g. (0.075 mol) sodium borohydride and following a procedure identical to that described in Example 1, 22 g. of the desired product (yield: 71.6%, referred to the diethyl aminomethylphosphonate) are obtained in the form of a light yellow oil.

IR (film), 3400–3240 cm$^{-1}$, 3000 cm$^{-1}$, 2900 cm$^{-1}$, 1600 cm$^{-1}$, 1510 cm$^{-1}$, 1240–1035 cm$^{-1}$, NMR (CDCl$_3$) δ/TMS 1.3 ppm (t, 6H), 3.2 ppm (m, 5H), after exchange with CD$_3$OD: (m, 4H), 3.95 ppm (qd, 4H), 7.2 to 8 ppm (m, 7H).

Stage e

2-(Naphth-1-yl)-ethylamine hydrochloride

By following the procedure described in Example 1, using the 22 g. of phosphoramidate obtained above, 11.6 g. (yield: 61%, referred to as the diethyl aminomethylphosphonate) of the desired hydrochloride are obtained in the form of white crystals; m.p. 260° C. (decomposition).

IR (KBr disc), 3400 cm$^{-1}$, 3050 cm$^{-1}$, 1600 cm$^{-1}$, 1510 cm$^{-1}$, 1495 cm$^{-1}$, 1400 cm$^{-1}$, 800 cm$^{-1}$, 775 cm$^{-1}$.

NMR (d$_6$-DMSO) δ/TMS, 3.4 ppm (m, 4H), 7.3 to 7.3 ppm (m, 7H), 8.65 ppm (m, 3H), exchangeable with D$_2$O.

Analysis: C$_{12}$H$_{13}$N.HCl (M.W. 207.69) calculated: C 69.39%; H 6.79%; N 6.74%; found: 69.44%; 6.76%; 6.54%.

EXAMPLE 6

Preparation of 2-(p-methoxyphenyl)-ethylamine hydrochloride

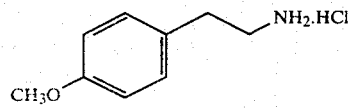

Stage a

Diethyl N-(p-methoxybenzylidene)-aminomethylphosphonate

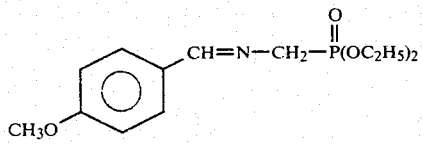

Starting from 16.7 g. (0.1 mol) diethyl aminomethylphosphonate and 13.6 g. (0.1 mol) p-methoxybenzaldehyde and following the procedure described in Example 1, 28.5 g. (yield: 100%) of the desired product are obtained in the form of a yellow oil.

IR (film) 1630 cm$^{-1}$, 1250 cm$^{-1}$, 1040 cm$^{-1}$,

| NMR (CDCl$_3$) δ/TMS | 1.3 ppm (t, 6H) |
| --- | --- |
| | 3.75 ppm (s, 3H) |
| | 4.15 ppm (m, 6H) |
| | 6.90 ppm (d, 2H) ⎫ A$_2$B$_2$ system |
| | 7.75 ppm (d, 2H) ⎭ |
| | 8.30 ppm (d, 1H) |

Stages b and c

Diethyl N-[β-(p-methoxyphenyl)-vinyl]-phosphoramidate

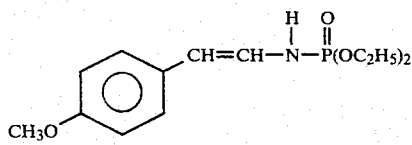

Starting from 28.5 g. (0.1 mol) of the imine prepared in the previous stage and following a procedure analogous to that described in Example 1, 20 g. (yield: 70%) of the desired product are obtained in the form of a yellow oil which is used as such in the following step.

Stage d

Diethyl N-[2-(p-methoxyphenyl)-ethyl]-phosphoramidate

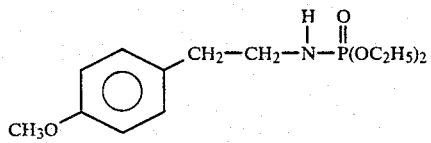

Starting from 20 g. (0.07 mol) of the vinylphosphoramidate prepared in the previous stages and 2.66 g. (0.07 mol) sodium borohydrate and by carrying out the reaction under conditions analogous to those described in Example 1, 20 g. (yield: 69.5%, referred to the diethyl aminomethylphosphonate) of the desired product are obtained in the form of an oil.

IR (film) 3400 cm$^{-1}$, 3240 cm$^{-1}$, 1240 cm$^{-1}$, 1035 cm$^{-1}$.

| NMR (CDCl$_3$) δ/TMS | 1.3 ppm (t, 6H) | |
| --- | --- | --- |
| | 3.2 ppm (m, 5H), | after exchange with CD$_3$OD: (m, 4H) |
| | 3.75 ppm (s, 3H) | |
| | 3.95 ppm (qd, 4H) | |
| | 6.90 ppm (d, 2H) ⎫ | A$_2$B$_2$ system |
| | 7.2 ppm (d, 2H) ⎭ | |

Stage e 2-(p-Methoxyphenyl)-ethylamine hydrochloride

By following the procedure described in Example 1 on the phosphoramidate obtained above, 8 g. (53%, referred to the starting aminomethylphosphonate) of the desired hydrochloride are obtained in the form of white crystals; m.p. 217° C.

IR (on the base as a film) 3350 cm$^{-1}$, 2950 cm$^{-1}$, 1610 cm$^{-1}$, 1510 cm$^{-1}$, 1210 cm$^{-1}$.

| NMR (D$_2$O) | 3.15 ppm (m, 4H) |
| --- | --- |
| | 3.8 ppm (s, 3H) |
| | 6.85 ppm (d, 2H) ⎫ AB system |
| | 7.3 ppm (d, 2H) ⎭ |
| | water peak at 4.75 ppm |

Analysis: C$_9$H$_{13}$NO.HCl (M.W. 187.66) calculated: C 57.59%; H 7.51%; N 7.46%; found: 57.55%; 7.48%; 7.50%.

EXAMPLE 7

Preparation of 2-(pyridin-4-yl)-ethylamine

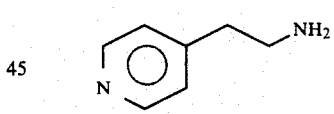

Stage a

Imine of pyridin-4-yl-carboxaldehyde and diethyl aminomethylphosphonate

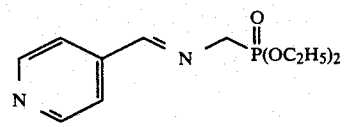

Starting from 10.7 g. (0.1 mol) pyridin-4-yl-carboxaldehyde and 16.7 g. (0.1 mol) diethyl aminomethylphosphonate and following the procedure described in Example 1, 25.6 g. (100%) of the desired product are prepared in the form of an orange oil.

IR (film), 1635 cm$^{-1}$, 1250 cm$^{-1}$, 1045 cm$^{-1}$.

| NMR (CDCl$_3$) | 1.3 ppm (t, 3H) |
| --- | --- |
| δ/TMS | 4.10 ppm (m, 6H) |

| | | |
|---|---|---|
| 7.7 ppm (d, 2H) | | A₂B₂ |
| 8.4 ppm (d, 1H) | N=CH—Ar | |
| 8.75 ppm (d, 2H) | | system |

Stages b and c

Diethyl N-[β-(pyridin-4-yl)-vinyl]-phosphoramidate

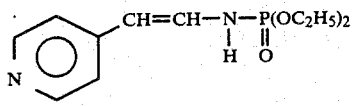

Starting from 25.6 g. (0.1 mol) of the imine prepared in stage (a) and following a procedure analogous to that described in Example 1, a crude product is isolated in the form of an orange oil which, after purification by chromatography on a silica column (eluant: 90% ethyl acetate/10% ethanol), gives 13 g. (yield: 50.7%) of the desired product in the form of orange crystals; m.p. 75° C.

IR (KBr disc) 3400 cm⁻¹, 3150 cm⁻¹, 1900 cm⁻¹, 1650 cm⁻¹, 1600 cm⁻¹, 1250–1040 cm⁻¹.

| NMR (CDCl₃ + D₂O) δ/TMS | 1.35 ppm | (t, 6H) | |
|---|---|---|---|
| | 4.15 ppm | (dq, 4H) | |
| | 5.80 ppm | (d, 1H) | J₁ = 15 Hz |
| | 7 ppm | (dd, 1H) | J₁ = 15 Hz |
| | | | J₂ = 19 Hz |
| | | | H—P coupling |
| | 6.95 ppm | (d, 2H) | } A₂B₂ system |
| | 8.25 ppm | (d, 2H) | |

Stage d

Diethyl N-[2-(pyridin-4-yl)-ethyl]-phosphoramidate

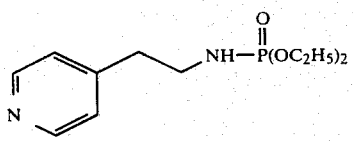

Reduction of the product obtained in the previous step with sodium borohydride, in accordance with the process described in Example 1, gives 13 g. (yield: 50.3%, referred to the starting aminomethylphosphonate) of the desired product in the form of an oil.

IR (film) 3400–3250 cm⁻¹, 1600 cm⁻¹, 1250 cm⁻¹, 1045 cm⁻¹,

| NMR (CDCl₃) | 1.3 ppm (t, 6H) | |
|---|---|---|
| | 3.2 ppm (m, 5H), | 1H exchangeable with D₂O |
| | 4.15 ppm (qd, 4H) | |
| | 7.9 ppm (d, 2H) | } A₂B₂ system |
| | 8.65 ppm (d, 2H) | |

Stage e 2-(Pyridin-4-yl)-ethylamine

Treatment of the phosphoramidate obtained in stage (d) with an aqueous solution of hydrochloric acid, under the conditions described in Example 1, gives, after rendering the mixture basic, 5.6 g. (yield: 47.5%, referred to the diethyl aminomethylphosphonate) of the desired amine in the form of a yellow oil which turns brown in air.

IR (film), 3300 cm⁻¹, 2900 cm⁻¹, 1600 cm⁻¹, 1440 cm⁻¹.

| NMR (DCl/D₂O) | 3.3 ppm (s, 4H) | |
|---|---|---|
| | 8 ppm (d, 2H) | } A₂B₂ system |
| | 8.7 ppm (d, 2H) | |

EXAMPLE 8

Preparation of 2-(furan-2-yl)-ethylamine hydrochloride

Stage a

Diethyl N-(furfuran-2-ylidene)-aminomethylphosphonate

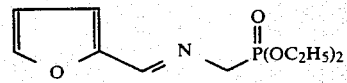

0.1 mol of the desired product is obtained in the form of a yellow oil by following the procedure described in Example 1.

IR (film) 1645 cm⁻¹, 1250 cm⁻¹, 1060 cm⁻¹, 1050 cm⁻¹.

NMR (CDCl₃) δ/TMS 1.3 ppm (t, 6H), 4 ppm (m, 6H), 7 to 7.5 ppm (m, 3H), 8.3 ppm (d, 1H).

Stages b and c

Diethyl N-[β-(furan-2-yl)-vinyl]-phosphoramidate

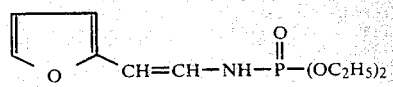

Starting from 0.1 mol of the above imine and by following the procedure described in Example 1, 18 g. of the desired product are obtained in the form of an oil which is used as such in the following stage.

Stage d

Diethyl N-[2-(furan-2-yl)-ethyl]-phosphoramidate

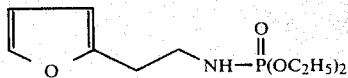

The vinyl phosphoramidate obtained above is reduced with sodium borohydride in accordance with the process described in Example 1. After purification by chromatography on a silica column (eluant: ethyl acetate), 14 g. (yield: 57%, referred to the aminomethylphosphonate) of the desired product are obtained in the form of a yellow oil.

NMR (D₂O) 3.25 ppm (m, 4H), 7.4 ppm (m, 4H), water peak at 4.5 ppm.

Analysis: C₈H₁₀NCl.HCl (M.W. 192.089) calculated: C 50.02%; H 5.77%; N 7.29%, found: 40.85%; 5.66%; 7.21%.

EXAMPLE 10

Preparation of 2-(thien-2-yl)-ethylamine hydrochloride

Stage a

Isopropyl N-(thien-2-ylidene)-aminomethyl-phenylphosphinate

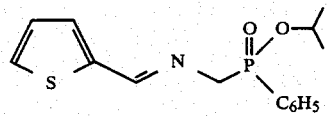

0.1 mol of the desired product is prepared by following the procedure described in Example 1.

IR (film) C=N 1625 cm⁻¹, 1430 cm⁻¹, 1200 cm⁻¹, 980 cm⁻¹.

NMR in CDCl₃ δ/TMS 1.4 ppm (dd, 6H), 4.15 ppm (d, 2H), 4.75 ppm (m, 1H), 7 to 8 ppm (m, 8H), 8.25 ppm (d, 1H).

Stages b and c

Isopropyl N-[β-(thien-2-yl)-vinyl]-amino-phenylphosphinate

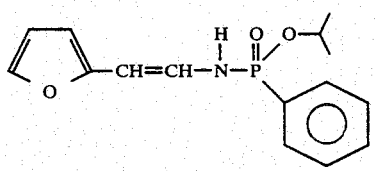

Starting from 0.1 mol of the imine prepared above and by following the procedure of Example 1, 18.6 g. (yield: 60.5%) of the desired product are obtained in the form of crystals; m.p. 125° C.

IR (KBr disc) 3400-3150 cm⁻¹ 1650 cm⁻¹ 1220 cm⁻¹ 1000 cm⁻¹

NMR (CDCl₃) δ/TMS 1.35 ppm (d, 6H), 4.8 ppm (m, 1H), 5.9 ppm (m, 1H), 6.2 to 7 ppm (m, 4H), 7 to 8 ppm (m, 6H), 1H exchangeable with D₂O.

Stage d

Isopropyl N-[2-(thien-2-yl)-ethyl]-amino-phenylphosphinate

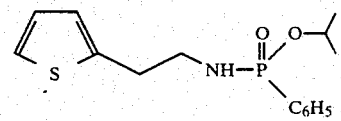

The compound obtained in the previous stage is reduced with sodium borohydride in alcohol, following the procedure of Example 1. This gives 18.6 g. (yield: 60.2%, referred to the aminomethyl-phenylphosphinate) of the desired phosphinate in the form of a light yellow oil.

IR (film) 3400 cm⁻¹, 3220 cm⁻¹, 2980 cm⁻¹, 2930 cm⁻¹, 2870 cm⁻¹, 1600 cm⁻¹, 1440 cm⁻¹, 1200 cm⁻¹, 990 cm⁻¹.

NMR (CDCl₃) δ/TMS 1.3 ppm, (dd, 6H), 3 ppm, (m, 5H), 1H exchangeable with D₂O, 4.65 ppm (m, 1H), 6.7 to 7.9 ppm (m, 8H).

Stage e 2-(Thien-2-yl)-ethylamine hydrochloride

The 18.6 g. of phosphinate obtained in stage (d) are treated overnight at ambient temperature with a solution of hydrogen chloride in diisopropyl ether to give 9 g. (yield: 55%, referred to the aminomethyl-phenylphosphinate) of 2-(thien-2-yl)-ethylamine hydrochloride, the physical, spectral and analytical characteristics of which are identical to those of the product obtained in Example 1.

We claim:

1. A multi-step process for the preparation of β-cyclo-substituted ethylamines of the formula:

$$Ar-CH_2-CH_2-NH_2 \quad (I)$$

in which Ar is selected from the group consisting of thienyl, furfuryl, pyridyl, phenyl and mono- or disubstituted thienyl, furfuryl, pyridyl, naphthyl and phenyl, wherein the substituent is selected from the group consisting of halogen nitro, amino, cyano, carboxyl, lower alkyl, haloloweralkyl, lower alkoxy, haloloeralkoxy and phenyl, which comprises condensing a compound of the formula:

in which X and Y, which may be the same or different, are lower alkyl, aryl, lower alkoxy, aryloxy, diloweralkylamino or diarylamino radicals, with a carbonyl compound of the formula:

$$Ar-CHO \quad (III)$$

in which Ar is as hereinbefore defined, to give a compound of the formula:

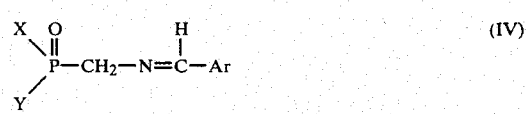

in which X, Y and Ar are as hereinbefore defined, treating the resultant compound with a base of the formula B⁻M⁺ to give a carbanion of the formula:

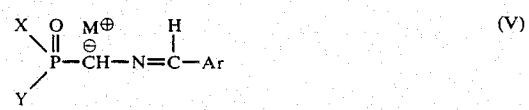

in which the X, Y and Ar are as hereinbefore described and M is alkyl, alkaline earth or alkali metals, heating the resulting compound so as to form a compound of the formula:

IR (film) 3400 cm⁻¹, 3250 cm⁻¹, 1600 cm⁻¹, 1510 cm⁻¹, 1240 cm⁻¹, 1060 cm⁻¹-1030 cm⁻¹, NMR (CDCl₃) 1.3 ppm (t, 6H), 3 ppm (m, 5H), after exchange with D₂O: (m, 4H), 4 ppm (dq, 4H), 6 ppm (d, 1H), 6.2 ppm (dd, 1H), 7.2 ppm (d, 1H).

Stage e 2-(Furan-2-yl)-ethylamine hydrochloride

A solution of the phosphoamidate obtained in the previous stage in 100 ml. of diisopropyl ether saturated with hydrogen chloride is stirred overnight at ambient temperature. The precipitate formed is isolated, redissolved in the minimum amount of ethanol and then reprecipitated by adding diisopropyl ether. After filtration and drying in vacuo, this gives 6.7 g. 2-(furan-2-yl)-ethylamine hydrochloride (yield: 45%, referred to the diethyl aminomethylphosphonate) in the form of white crystals; m.p. 204° C.

IR (KBr disc), 2800 to 3200 cm⁻¹, 1600 cm⁻¹, 1580 cm⁻¹, 1500 cm⁻¹, 1210 cm⁻¹, 1220 cm⁻¹, 1140 cm⁻¹, 1150 cm⁻¹, NMR (D₂O), 3.15 ppm (m, 4H), 6.3 ppm (d, 1H), 6.45 ppm (dd, 1H), 7.5 ppm (d, 1H).

Analysis: C₆H₉NO.HCl (M.W. 147.6) calculated: C 48.82%; H 6.82%; N 9.49%; found: 48.70%; 6.90%; 9.40%.

EXAMPLE 9

Preparation of 2-(o-chlorophenyl)-ethylamine hydrochloride

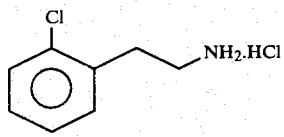

Stage a

Diethyl N-(o-chlorobenzylidene)-aminomethylphosphonate

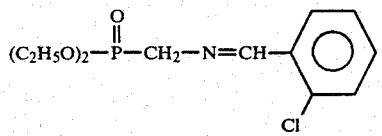

14 g. (0.1 mol) 2-Chlorobenzaldehyde are added dropwise at ambient temperature to a solution of 16.7 g. (0.1 mol) diethyl aminomethylphosphonate in 200 ml. toluene. When the addition has ended, stirring is continued for 30 minutes. The water formed during the reaction is removed by decantation. The toluene phase is washed with 50 ml. of a saturated aqueous solution of sodium chloride, dried over anhydrous sodium sulphate and then evaporated to give 29 g. (yield: 100%) diethyl N-(o-chlorobenzylidene)-aminomethylphosphonate in the form of a yellow oil giving a single spot in TLC (silica plate, eluant: AcOEt, rf=0.45).

IR (film) C=N 1635 cm⁻¹, P=O 1250 cm⁻¹, P—O—C 1060 cm⁻¹-1030 cm⁻¹,

NMR (CDCl₃)/TMS 1.35 ppm (t, 6H), 4.2 ppm (m, 6H), 7.1 to 7.5 ppm (m, 3H), 8 ppm (m, 1H), 8.7 ppm (d, 1H),

Stages b and c

Diethyl N-[β-(o-chlorophenyl)-vinyl]-phosphoramidate

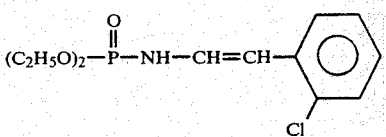

28.95 g. (0.1 mol) of the imine prepared above, dissolved in 40 ml. tetrahydrofuran are added dropwise to a suspension of 4.8 g. (0.1 mol) sodium hydride (50% dispersion in oil) in 100 ml. tetrahydrofuran. After the end of the addition, during which the temperature rises from 20° to 30° C., the mixture is heated at 45° C. for 2 hours. After it has again cooled to ambient temperature, the reaction mixture is hydrolysed by pouring it into 500 ml. of a saturated aqueous solution of ammonium chloride, followed by extraction with diisopropyl ether. The combined ether phases are washed with a saturated solution of sodium chloride, dried over anhydrous sodium sulphate and then evaporated to give a yellow oil which solidifies upon trituration in hexane. After the precipitate has been filtered off, washed with a diisopropyl ether/hexane mixture (10/90 v/v) and dried in vacuo, 21.7 g. (yield: 75%, referred to the diethyl aminomethylphosphonate) diethyl N-[β-(o-chlorophenyl)-vinyl]-phosphoramidate are obtained in the form of yellow crystals; m.p. 98° C.

IR (KBr disc) 3400 cm⁻¹, 3150 cm⁻¹, 1650 cm⁻¹, 1430 cm⁻¹, 1240 cm⁻¹, 1020 cm⁻¹,

NMR (CDCl₃) δ/TMS 1.3 ppm (t, 6H) 4.1 ppm (dq, 4H) 6 to 6.5 ppm (m, 2H) 6.8 to 7.5 ppm (m, 5H)

Analysis: C₁₂H₁₇ClNO₃P (M.W. 289.7) calculated: C 49.74%; H 5.91%; N 4.83%, found: 49.54%; 5.9%; 4.80%.

Stage d

Diethyl N-[2-(o-chlorophenyl)-ethyl]-phosphoramidate

Starting from 0.05 mol of the phosphoramidate prepared above and 0.05 mol sodium borohydride and by following the procedure of Example 1, 14.6 g. (yield of the reduction: 100%) diethyl N-[2-(o-chlorophenyl)-ethyl]-phosphoramidate are obtained in the form of a colourless oil.

IR (film) 3300 cm⁻¹, 1250 cm⁻¹, 1050 cm⁻¹,

NMR (CDCl₃) δ/TMS 1.3 ppm (t, 6H), 3 ppm (m, 5H), after exchange with CD₃OD: (m, 4H), 4 ppm (qd, 4H), 7.2 ppm (m, 4H),

Stage e 2-(o-Chlorophenyl)-ethylamine hydrochloride

The phosphoramidate obtained above is treated with aqueous hydrochloric acid under the conditions described in Example 1 to give the desired amine, after the mixture has been rendered basic and extracted with diisopropyl ether; this amine is converted into its hydrochloride by adding an ethanolic solution of hydrogen chloride. After the precipitate formed has been filtered off, washed with diisopropyl ether and dried at 50° C. in vacuo, 8.65 g. (yield: 90%) 2-(o-chlorophenyl)ethylamine hydrochloride are obtained in the form of white crystals; m.p. 145° C.

IR (KBr disc) 3300 cm⁻¹, 2900 to 3000 cm⁻¹, 1575 cm⁻¹, 1475-1450 cm⁻¹, 1230 cm⁻¹.

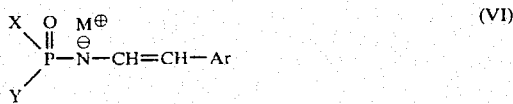

in which X, Y, M+ and Ar are as hereinbefore described, treating the compound formed with water so as to yield a compound of the formula:

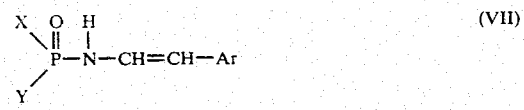

in which X, Y and Ar are as hereinbefore described, treating the resulting compound with a reducing agent to give a compound of the formula:

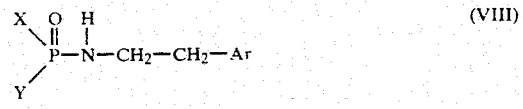

in which X, Y and Ar are as hereinbefore described, and then reacting the resulting compound with an acid to give a compound of formula (I).

2. The process according to claim 1, wherein the conversion of the carbanion of the formula (V) to a compound of the formula (VI) is carried out at a temperature of from −78° C. to +150° C.

3. The process according to claim 2, wherein the reaction is carried out at a temperature which is chosen as a function of the base to be on the whole at the top of the range.

4. The process according to claim 2, wherein the reaction is carried out in an organic solvent.

5. The process according to claim 4, wherein the organic solvent is selected from the group consisting of a linear or cyclic ether, an aromatic hydrocarbon, an alcohol or an amide.

6. The process according to any of claims 1, 2, 3, 4 or 5, wherein the reduction of the compound of formula (VII) is carried out by means of an alkali metal borohydride.

7. The process according to claim 6, wherein the alkali metal borohydride is sodium or potassium borohydride.

8. The process according to claim 1 in which 2-(5-bromothien-2-yl)-ethylamine is prepared.

9. The process according to claim 1 in which Ar is an aromatic radical selected from the group consisting of thienyl, furfuryl, pyridyl, phenyl and naphthyl.

10. The process according to claim 9 in which the aromatic radical is phenyl.

11. The process according to claim 9 wherein the aromatic radical is mono- or di-substituted with a member selected from the group consisting of halogen, nitro, amino cyano, carboxyl, lower alkyl, monohalogenloweralkyl, lower alkoxy, monohalogen-loweralkoxy and phenyl.

* * * * *